United States Patent [19]

Slongo et al.

[11] Patent Number: 5,030,731
[45] Date of Patent: Jul. 9, 1991

[54] COATING MATERIAL STABILIZED AGAINST THE ACTION OF LIGHT

[75] Inventors: Mario Slongo, Tafers; Manfred Rembold, Aesch, both of Switzerland

[73] Assignee: Ciba-Geigy Corporation, Ardsley, N.Y.

[21] Appl. No.: 427,919

[22] Filed: Oct. 24, 1989

Related U.S. Application Data

[60] Continuation of Ser. No. 215,104, Jul. 5, 1988, abandoned, which is a division of Ser. No. 65,655, Jun. 22, 1987, Pat. No. 4,775,707, which is a continuation of Ser. No. 792,075, Oct. 28, 1985, abandoned.

[30] Foreign Application Priority Data

Nov. 1, 1984 [CH] Switzerland ............... 5220/84
Feb. 1, 1985 [CH] Switzerland ............... 453/85

[51] Int. Cl.$^5$ ............... C07D 249/16; C07D 403/00
[52] U.S. Cl. ............... 548/260; 548/261
[58] Field of Search ............... 548/261

[56] References Cited

U.S. PATENT DOCUMENTS 3,600,397  8/1971  Seki et al. ............... 524/91
4,247,628  1/1981  Uchida et al. ............... 430/551
4,775,707 10/1988  Slongo et al. ............... 524/91

Primary Examiner—Kriellion Morgan
Attorney, Agent, or Firm—Luther A. R. Hall

[57] ABSTRACT

Blocked benzotriazoles of the formula I or II

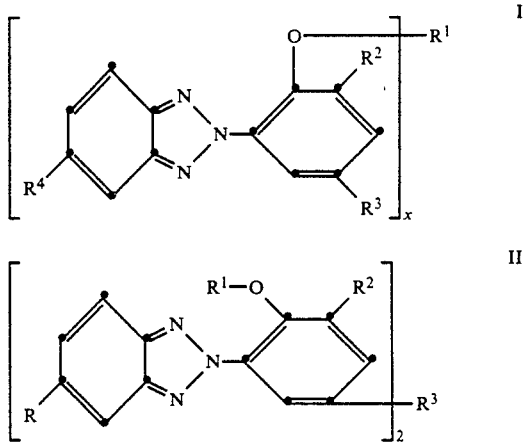

wherein x is 1 or 2,
$R^1$ in the case of x=1 and in the formula II is an acyl group of the formula —CO—$R^5$, a sulfonyl group of the formula —SO$_2$—$R^6$, a phosphoryl group of the formula —P(O)$_r$($R^{14}$)($R^{15}$), and in the case of x=2 is —CO— or a diacyl group of the formula —CO—CO— or —CO—$R^7$—CO—, and $R^2$, $R^3$, $R^4$, $R^5$, $R^6$, $R^7$, $R^{14}$ and $R^{15}$ have the meanings defined in claim 1, are crypto light stabilizers which can be activated by short-wave irradiation. Their use in coating materials is of interest in cases in which light stabilizers containing the free OH compounds have disadvantages with regard to their application.

4 Claims, No Drawings

COATING MATERIAL STABILIZED AGAINST THE ACTION OF LIGHT

This application is a continuation of Ser. No. 215,104, filed on July 5, 1988, now abandoned, which is in turn a divisional of Ser. No. 065,655, filed on June 22, 1987, now U.S. Pat. No. 4,775,707, issued on Oct. 4, 1988, which is in turn a continuation of Ser. No. 792,075, filed on Oct. 28, 1985, now abandoned.

The invention relates to coating materials containing crypto light stabilisers. Such compounds are activated by the action of short-wave light in that they are converted photochemically into light stabilisers. The compounds concerned are specific derivatives of 2-(2-hydroxyphenyl)-benzotriazoles having a blocked hydroxyl group.

Olson and Schroeter (J. Appl. Pol. Science 22 (1978), 2165–72) have already suggested blocking the phenolic hydroxyl group of 2-(2-hydroxyphenyl)-benzotriazoles with chemical protective groups which are subsequently removable, for example by hydrolysis, photolysis or heating. These blocked benzotriazole derivatives do not absorb in the UV range of 330–400 nm and as a result do not disturb the photopolymerisation of UV-curable compositions. Because of their changed UV-absorption level (their absorption maximum is about 290–310 nm), they are however not suitable as light stabilisers, and have therefore to be converted after photopolymerisation into the benzotriazoles having a free OH group, which are known light stabilisers. The stated authors investigated the possibility of blocking the OH group by silylation, by carbamoylation and, in a later work (J. Appl. Pol. Science 28 (1983), 1159 –65), also by etherification, esterification and sulfonylation. Various problems arise in this connection, such as insufficient cleavage or discoloration resulting from the formation of by-products. The O-sulfonylation and photochemical cleavage are described as being the best methods. In the case of this cleavage, there occurs essentially a photochemical Fries rearrangement to the ortho-sulfonylphenols. This is possible because all examined compounds are unsubstituted in the ortho-position (with respect to the OH group).

It has now been found that with the use of 2-(2-hydroxyphenyl)-benzotriazoles, which are substituted both in the para-position and in the ortho-position with respect to the OH group, there are obtained, by blocking of the OH group, crypto light stabilisers which have an absorption maximum likewise at 290-310 nm but which, in spite of the substitution in the para-position and in the ortho-position, can be photochemically reconverted into compounds having a free OH group.

They have a level of stability in darkness which is higher than that of the compounds having an unsubstituted ortho-position. This factor is important with respect to the commercial application, since lacquers are frequently stored for long periods.

Compared with the known benzotriazole light stabilisers having a free OH group, these crypto light stabilisers are of advantage when the coating material is in contact with metals before or during application. All 2-(2-hydroxyphenyl)-benzotriazoles form with metal ions complexes which are often coloured (for example in the case of Cu, Ni or Co), and they can then cause a discoloration of the coating material. Another interesting field of application for crypto light stabilisers is that covering oxidatively drying coating materials which contain, as curing catalysts (siccatives), organic metal compounds. In the presence of free 2-(2-hydroxyphenyl)-benzotriazoles, these metal compounds are bound by coordination to the benzotriazole, and are then no longer effective as curing catalysts.

The present invention thus relates to coating materials containing, as a crypto light stabiliser, a compound of the formula I or II

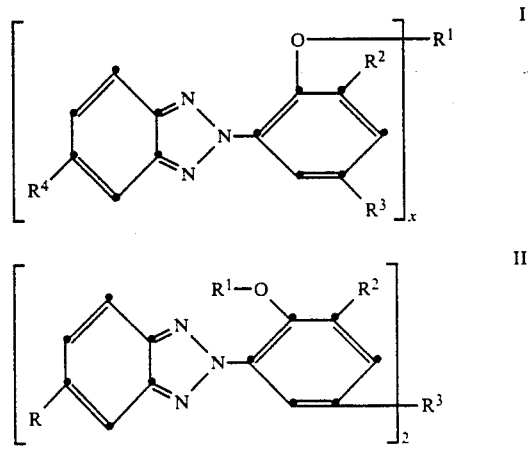

wherein x is 1 or 2,

R$^1$ in the case of x=1 and in the formula 11 is an acyl group of the formula —CO—R$^5$, a sulfonyl group of the formula —SO$_2$—R$^6$, a phosphoryl group of the formula —P(O)$_r$(R$^{14}$) (R$^{15}$ of x=2 is —CO— or a diacyl group of the formula —CO—CO— or —CO—R —CO—, R$^2$ is C$_1$-C$_{12}$-alkyl, C$_5$-C$_{12}$-cycloalkyl, phenyl, C$_7$-C$_9$-phenylalkyl, C$_3$-C$_5$-alkenyl or halogen, R$^3$ in the formula I is C$_1$-C$_{12}$-alkyl, C$_5$-C$_{12}$-cycloalkyl, phenyl, C$_7$-C$_9$-phenylalkyl, halogen or a group of the formula —(CH$_2$)$_n$—COOR$^9$ or —(CH$_2$)$_n$—CO—N(R$^{10}$) (R$^{11}$), and in the formula 11 is a divalent radical of the formula:

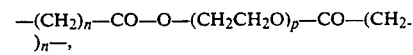

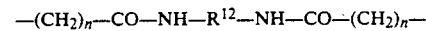

or

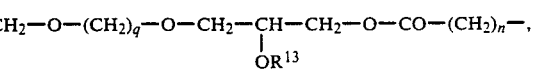

R$^4$ is hydrogen, halogen, C$_1$-C$_8$-alkyl, C$_7$-C$_9$-phenylalkyl, C$_1$-C$_8$-alkoxy or C$_2$-C$_8$-alkoxycarbonyl, R$^5$ is C$_1$-C$_{18}$-alkenyl —CH$_2$—CO—CH$_3$, phenyl, phenyl substituted by C$_1$-C$_{12}$-alkyl, C$_1$-C$_4$-alkoxy or benzoyl, C$_7$-C$_{12}$-arylalkyl or C$_1$-C$_{12}$-alkoxy, R$^6$ is C$_1$-C$_{12}$-alkyl, C$_6$-C$_{10}$-aryl or C$_7$-C$_{18}$-alkylaryl, R$^7$ is C$_1$-C$_{10}$-alkylene or phenylene, $R^9$ is hydrogen, $C_1$-$C_{12}$-alkyl or a group of the formula —$(CH_2CH_2O)_p$—$R^1$, $R^{10}$ and $R^{11}$ independently of one another are hydrogen, $C_1$-$C_{12}$-alkyl, which can be interrupted by O or N, $C_5$-$C_{12}$-cycloalkyl, $C_7$-$C_9$-phenylalkyl, $C_3$-$C_5$-alkenyl, phenyl or a 2,2,6,6-tetramethyl-4-piperidinyl radical, or $R^{10}$ and $R^{11}$ together are $C_4$-$C_6$-alkylene, -oxaalkylene or -azaalkylene, $R^{12}$ is $C_1$-$C_{12}$-alkylene, which can be interrupted by 1–3 O atoms, $R^{13}$ is $C_1$-$C_{12}$-alkyl or $C_6$-$C_{10}$-aryl, $R^{14}$ and $R^{15}$ independently of one another are each $C_1$-$C_{12}$-alkoxy, phenoxy, $C_1$-$C_{12}$-alkyl, cyclohexyl, benzyl, phenyl or tolyl, n is 1 or 2, p is a number from 1 to 10, q is a number from 2 to 12, and r is 0 or 1.

As a monovalent acyl group $R^1$ can be for example: acetyl, propionyl, butyryl, valerianyl, capronyl (n-hexanoyl), 2-ethylhexanoyl, capryloyl (n-octanoyl), caprionyl (n-decanoyl), lauroyl (n-dodecanoyl), palmityl (n-hexadecanoyl), stearoyl (n-octadecanoyl), acryloyl, methacryloyl, crotonyl, oleyl, linoleyl, benzoyl, 3-methylbenzoyl, 4-tert-butylbenzoyl, 4-hexylbenzoyl, 4-dodecylbenzoyl, 3- or 4-methoxy- or -ethoxybenzoyl, 4-benzoylbenzoyl, phenylacetyl, phenylpropionyl, naphthylacetyl, methoxycarbonyl, ethoxycarbonyl, butoxycarbonyl, octyloxycarbonyl or dodecyloxycarbonyl. Examples of $R^1$ as a sulfonyl group are the groups: methyl-, tert-butyl-, octyl-, dodecyl-, phenyl-, tolyl-, naphthyl-, 4-nonylphenyl-, 4-dodecylphenyl- or mesitylenesulfonyl.

$R^1$ as a diacyl group can be for example: oxalyl, succinyl, glutaroyl, adipoyl, 2,2,4-trimethyladipoyl, sebacoyl (octamethylenedicarbonyl), decamethylenedicarbonyl, terephthaloyl or isophthaloyl. $R^2$, $R^3$, $R^4$, $R^9$, $R^{10}$, $R^{11}$, $R^{13}$, $R^{14}$, $R^{15}$ as alkyl can, within the given number of C atoms, be for example: methyl, ethyl, propyl, isopropyl, n-butyl, isobutyl, sec-butyl, tert-butyl, pentyl, hexyl, heptyl, octyl, decyl or dodecyl.

$R^2$ and $R^3$ are preferably branched-chain alkyl groups.

$R^{10}$ and $R^{11}$ as alkyl interrupted by O or N can be for example: 2-butoxyethyl, 3-methoxypropyl, 3-ethoxypropyl, 3-isopropoxypropyl, 3-butylaminopropyl or 3-ethylaminopropyl.

$R^2$, $R^{10}$ and $R^{11}$ as alkenyl can be for example: allyl, methallyl or 2-butenyl.

$R^{14}$ and $R^{15}$ as alkoxy can be for example: methoxy, ethoxy, isopropoxy, butoxy, hexyloxy, octyloxy, decyloxy or dodecyloxy.

$R^2$ and $R^3$ halogen can be for example: fluorine, chlorine or bromine.

$R^2$, $R^3$, $R^{10}$ and $R^{11}$ as cycloalkyl can be for example: cyclopentyl, cyclohexyl, methylcyclohexyl, cyclooctyl or cyclododecyl.

$R^2$, $R^3$, $R^{10}$ and $R^{11}$ as phenylalkyl can be for example: benzyl, α-methylbenzyl, α-dimethylbenzyl or 2-phenylethyl. $R^2$ and $R^3$ lalkyl are preferably α-dimethylbenzyl.

$R^4$ as alkoxy or alkoxycarbonyl can be for example: methoxy, ethoxy, isopropoxy, butoxy, hexyloxy, octyloxy, methoxycarbonyl, ethoxycarbonyl, butoxycarbonyl or pentyloxycarbonyl. $C_1$-$C_4$-alkoxy or alkoxycarbonyl radicals are preferred.

$R^7$ as alkylene can be for example: methylene, 1,2-ethylene, tri-, tetra-, penta-, hexa-, octa- or decamethylene.

When $R^{10}$ and $R^{11}$ together are alkylene, oxa- or azaalkylene, they form together with the N atom to which they are bound a heterocyclic ring, for example a pyrrolidine, piperidine, morpholine, piperazine or hexamethylene ring.

$R^{12}$ can be for example: 1,2-ethylene, tri-, tetra-, penta-, hexa-, octa- or dodecamethylene, 2,4,4-trimethylhexamethylene, 3-oxaheptamethylene or 3,6-dioxadecamethylene.

Preferred compounds of the formula I are those wherein x=1, $R^1$ is a group of the formula —CO—$R^5$, —$SO_2$—$R^6$ or —P(O)($R^{14}$)($R^{15}$), $R^2$ is $C_1$-$C_{12}$—alkyl, cyclohexyl or $C_7$-$C_9$-phenylalkyl, $R^3$ is $C_1$-$C_{12}$-alkyl, cyclohexyl, $C_7$-$C_9$-phenylalkyl or a group —$CH_2CH_2COOR^9$, $R^4$ is hydrogen, methyl or chlorine, $R^5$ is $C_1$-$C_{12}$-alkyl, $C_2$-$C_4$-alkenyl, phenyl, benzyl or naphthylmethyl, $R^6$ is methyl, phenyl or $C_7$-$C_{18}$-alkylphenyl, $R^9$ is $C_1$-$C_{12}$-alkyl, and $R^{14}$ and $R^{15}$ independently, of one another are each $C_1$-$C_4$-alkoxy, methyl or phenyl. Preferably, $R^1$ therein is a group —CO—$R^5$ or —$SO_2$—$R^6$, $R^2$ is $C_1$-$C_8$-alkyl or α-dimethylbenzyl, $R^3$ is $C_1$-$C_8$-alkyl, α-dimethylbenzyl or a group —$CH_2CH_2COOR^9$, and $R^4$ is hydrogen or chlorine.

Particularly preferred compounds of the formula I are those wherein x=1, $R^1$ is a group —CO—$R^5$ or —$SO_2$—$R^6$, $R^2$ is $C_1$-$C_8$-alkyl or α-dimethylbenzyl, $R^3$ is $C_1$-$C_8$-alkyl, α-dimethylbenzyl or —$CH_2CH_2COOR^9$, $R^4$ is hydrogen or chlorine, $R^5$ is $C_1$-$C_{12}$-alkyl, $C_2$-$C_4$-alkenyl, phenyl, benzyl or naphthylmethyl, $R^6$ is methyl, phenyl or $C_7$-$C_{18}$-alkylphenyl, and $R^9$ is $C_1$-$C_{12}$-alkyl.

Preferred also are compounds of the formula I wherein x=2, $R^1$ is a group —CO—$R^7$—CO—, $R^2$ is $C_1$-$C_8$-alkyl or α-dimethylbenzyl, $R^3$ is $C_1$-$C_8$-alkyl, α-dimethylbenzyl or a group —$CH_2CH_2COOR^9$, $R^4$ is hydrogen or chlorine, $R^7$ is $C_2$-$C_8$-alkylene, and $R^9$ is $C_{1-C_{12}}$-alkyl.

Further preferred compounds are those of the formula II wherein $R^1$ is a group —CO—$R^5$ or —$SO_2$—$R^6$, $R^2$ is $C_1$-$C_8$-alkyl or α-dimethylbenzyl, $R^3$ is a group of the formula —$CH_2CH_2COO$—$(CH_2)_q$—$OCOCH_2CH_2$— or —$CH_2CH_2CONH$—$R^{12}$—$NHCOCH_2CH_2$—, $R^4$ is hydrogen or chlorine, $R^5$ is $C_1$-$C_{12}$-alkyl, $C_2$-$C_4$-alkenyl, phenyl, benzyl or naphthylmethyl, $R^6$ is methyl, phenyl or $C_7$—$C_{18}$-alkylphenyl, $R^{12}$ is $C_2$—$C_8$-alkylene, and q is a number from 2 to 8.

Some of these compounds are known and some are novel compounds. They can be produced essentially from the corresponding hydroxyl compounds ($R^1$=H) by esterification of the hydroxyl group, using the customary methods of acylation of phenolic OH groups, for example by reaction with carboxylic acid anhydrides, carboxylic acid chlorides, sulfonic acid chlorides or chlorophosphates. Examples of these are given in the subsequent production examples. The hydroxyl compounds used as starting materials are in part obtainable commercially, or can be produced by the methods generally known for the production of 2-(2-hydroxyphenyl)-benzotriazoles.

Novel compounds are for example those compounds of the formula I wherein $R^3$ is a group —$(CH_2)_n$—$COOR^9$ or —$(CH_2)_n$—$CON(R^{10})(R^{11})$; and also compounds of the formula II wherein $R^3$ is a divalent group of the formula

$-(CH_2)_n-CO-O-(CH_2CH_2O)_p-CO-(CH_2)_n-$, $-(CH_2)_n-CO-NH-R^{10}-NH-CO-(CH_2)_n-$ or $-(CH_2)_n-CO-O-CH_2-\underset{OR^{11}}{CH}-CH_2-O-(CH_2)_q-O-CH_2-\underset{OR^{11}}{CH}-CH_2-O-CO-(CH_2)_n-$.

Examples of individual compounds of the formula I are:
2-(2-acetoxy-3-methyl-5-tert-butyl-phenyl)-benzotriazole,
2-[2-acetoxy-3,5-di(tert-butyl)-phenyl]-benzotriazole,
2-(2-propionyloxy-3-isopropyl-5-tert-butyl-phenyl)-benzotriazole,
2-(2-butyroyloxy-3-sec-butyl-5-tert-butyl-phenyl)-benzotriazole,
2-[2-hexanoyloxy-3,5-di(tert-pentyl)-phenyl]-benzotriazole,
5-chloro-2-2-octanoyloxy-3,5-di(tert-butyl)-phenyl]benzotriazole,
5-methyl-2-(2-benzoyloxy-3,5-dimethyl-phenyl)-benzotriazole,
5-methoxy-2-[2-(4-chlorobenzoyloxy)-3,5-di(tert-butyl)phenyl-benzotriazole,
2-2-p-toluenesultonyloxy-3,5-di(tert-butyl)-phenyl]benzotriazole
2-2-dodecylsulfonyloxy-3,5-di(1,1.dimethylbenzyl)-phenyl]benzotriazole,
2-[2-(p-dodecylbenzenesulfonyloxy)-3-sec-butyl-5-tert-butylphenyl]-benzotriazole,
di-[2-(benzotriazol-2-yl)-4,6-di(tert-butyl)-phenyl]adipate,
di-[2-(5-chlorobenzotriazol-2-yl)-4-methyl-6-tert-butylphenyl]-isophthalate,
β-[3-(benzotriazol-2-yl)-4-acetoxy-5-tert-butyl-phenyl]-propionic acid methyl ester,
[3-(benzotriazol-2-yl)-4-p-toluenesulfonyloxy-5-tert-butylphenyl]-acetic acid butyl ester, and
-[3-(benzotriazol-2-yl)-4-benzoyloxy-5-cyclohexyl-phenyl]propionic acid-2-butoxyethyl ester.

Examples of individual compounds of the formula II are: di-[3-(benzotriazol-2-yl)-4-acetoxy-5-tert-butyl-phenylacetic acid ester] of diethylene glycol,
di-[β-(3-(benzotriazol-2-yl)-4-p-toluenesulfonyloxy-5-secbutyl-phenyl)-propionic acid ester] of butanediol-1,4, and
N,N'-hexamethylene-bis[β-(3-(benzotriazol-2-yl)-4butyroyloxy-5-methyl-phenyl)-propionic acid amide].

The following Examples further illustrate the production of compounds such as those listed above.

PRODUCTION EXAMPLES

Example A - Acetylation 100 ml of acetic anhydride are added to 1 mol of 5-chloro-2-[2-hydroxy-3,5-di(tert-butyl)-phenyl]-benzotriazole, and the mixture is refluxed (140° C.). After the addition of 0.6 g of dimethylaminopyridine, the mixture is refluxed for a further 7 hours. A specimen shows in the thin-layer chromatogram that no further starting material is present. The excess acetic anhydride is distilled off in vacuo, and the brown residue is dissolved in methylene chloride. The solution is washed with a 5% $Na_2CO_3$ solution and with water; it is then dried over $Na_2SO_4$ and concentrated by evaporation. The crystalline residue is recrystallised from methanol to thus obtain 5-chloro-2-[2-acetoxy-3,5-di(tert-butyl)-phenyl]-benzotriazole in the form of white crystals which melt at 132°-134° C. (compound No. 1).

There are obtained in an analogous manner the following acetoxy compounds of the general formula

| Compound No. | $R^2$ | $R^3$ | $R^4$ | Physical constants |
|---|---|---|---|---|
| 2 | tert.-butyl | $-CH_2CH_2COOCH_3$ | H | m.p. 67–69° (from ligroin) |
| 3 | tert.-butyl | $-CH_2CH_2COOC_8H_{17}$ (mixture of n- and iso-octyl) | Cl | oil<br>C cal. 65.8% found 66.1%<br>H cal. 7.4% found 7.2%<br>N cal. 7.9% found 8.1% |
| 4 | tert.-butyl | $-CH_2CH_2COOCH_2CH_2OC_2H_5$ | H | viscous resin<br>C cal. 63.4% found 63.4%<br>H cal. 6.5% found 6.5%<br>N cal. 8.2% found 8.2% |
| 5 | tert.-butyl | tert.-butyl | H | m.p. 155–157° (from ligroin) |
| 6 | tert.-pentyl (1,1-dimethylpropyl) | tert.-pentyl | H | m.p. 121–122° (from ligroin) |
| 7 | sec.-butyl | tert.-butyl | H | viscous resin<br>C cal. 72.3% found 72.3%<br>H cal. 7.4% found 7.4%<br>N cal. 11.5% found 11.5% |
| 8 | α-dimethylbenzyl | α-dimethylbenzyl | H | m.p. 180–182° (from toluene) |
| 9 | tert.-butyl | $-CH_2CH_2CONH(CH_2)_6NHCOCH_2CH_2-$ | H | m.p. 87–90° C. |
| 10 | tert.-butyl | $-CH_2CH_2COOH$ | H | m.p. 134–136° C. |

Example B - Tosylation 0.1 mol of 2-(2-hydroxy-3-sec-butyl-5-tert-butylphenyl)benzotriazole is dissolved in 200 ml of toluene. There is then added, with stirring, a solution of 20 g of NaOH in 20 g of water and 0.01 mol of tetrabutylammonium hydrogen sulfate (as phase-transfer catalyst), in the course of which the organic phase assumes an intense yellowish-orange colour. A solution of 0.11 mol of p-toluenesulfonyl chloride in 50 ml of toluene is then slowly added dropwise at room temperature. The exothermic reaction is compensated for by cooling with ice-water. The mixture is subsequently stirred for 3 hours at room temperature, during which time the colour of the toluene solution gradually disappears. A specimen indicates in the thin-layer chromatogram that no further starting material is present. The reaction mixture is poured into 1 litre of ice-water; the organic phase is separated, washed twice with 300 ml of water each time and dried over Na₂SO₄. The solution is concentrated in vacuo, and the residue is crystallised from ethanol to thus obtain 2-(2-toluenesulfonyloxy-3-sec-butyl-5-tert-butylphenyl)-benzotriazole in the form of white crystals which melt at 139°–141° C. (compound No. 11).

There are obtained in an analogous manner the following sulfonates of the general formula The bis-tosylate of the following formula is produced in an analogous manner:

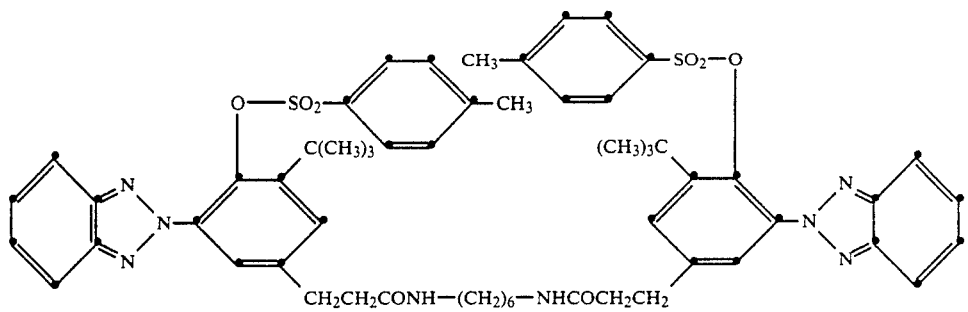

(compound No. 24) m.p.: 215–217° C.

Example C - Esterification with acid chloride 0.12 mol of triethylamine is added to a solution of 0.08 mol of 2-[2-hydroxy-3,5-di(tert-butyl)-phenyl]-benzotriazole in 150 ml of methylene chloride. To this solution is slowly added dropwise at 10°–15° C., with stirring, a solution of 0.08 mol of 2-naphthylacetyl chloride in 50 ml of methylene chloride. The temperature is then allowed to rise to 20°–25° C., and the mixture is stirred for 6 hours at this temperature. The triethylammonium chloride which has precipitated is filtered off, and the filtrate is washed with water, dried over Na₂SO₄ and concentrated by evaporation. The crystalline, reddish-coloured residue is recrystallised from hexane to thus obtain 2-[2-(1-naphthylacetoxy)-3,5-di(tert-butyl)-phenyl]-benzotriazole in the form of white crystals which melt at 150°–151° C. (compound No. 25).

There are obtained in an analogous manner the following phenol esters of the general formula

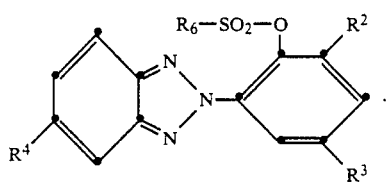

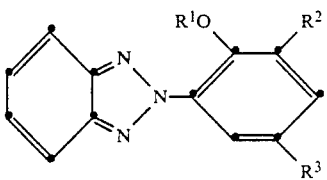

| Compound No. | R² | R³ | R⁴ | R⁶ | Physical constants | | | |
|---|---|---|---|---|---|---|---|---|
| 12 | tert.-butyl | tert.-butyl | H | p-tolyl | m.p. 187–189° (from ethanol) | | | |
| 13 | tert.-pentyl | tert.-pentyl | H | p-tolyl | m.p. 152–154° (from ethanol) | | | |
| 14 | α-dimethylbenzyl | α-dimethylbenzyl | H | p-tolyl | m.p. 152–154° (from isopropanol) | | | |
| 15 | tert.-butyl | —CH₂CH₂COOCH₃ | H | p-tolyl | m.p. 123–125° (from methanol) | | | |
| 16 | tert.-butyl | —CH₂CH₂COOC₈H₁₇ (mixture of n- and iso-octyl) | Cl | | C | cal. 63.8% | found | 64.1% |
| | | | | | H | cal. 6.6% | found | 6.6% |
| | | | | | N | cal. 6.6% | found | 6.8% |
| | | | | | Cl | cal. 5.5% | found | 5.5% |
| | | | | | S | cal. 5.0% | found | 4.9% |
| 17 | tert.-pentyl | tert.-pentyl | H | p-dodecyl-phenyl | C | cal. 72.8% | found | 72.7% |
| | | | | | H | cal. 8.7% | found | 8.7% |
| | | | | | N | cal. 6.4% | found | 6.5% |
| 18 | tert.-butyl | tert.-butyl | H | p-dodecyl-phenyl | C | cal. 72.3% | found | 72.0% |
| | | | | | H | cal. 8.5% | found | 8.5% |
| | | | | | N | cal. 6.7% | found | 6.8% |
| 19 | tert.-butyl | tert.-butyl | H | methyl | m.p. 149–151° | | | |
| 20 | tert.-pentyl | tert.-pentyl | H | methyl | m.p. 88–90 | | | |
| 21 | tert.-butyl | —CH₂CH₂COOCH₃ | H | methyl | m.p. 142–144° | | | |
| 22 | α-dimethylbenzyl | α-dimethylbenzyl | H | methyl | m.p. 176–178° | | | |
| 23 | sec.-butyl | tert.-butyl | H | p-tolyl | m.p. 139–141° C. | | | |

| Compound No. | R¹ | R² | R³ | Physical constants |
|---|---|---|---|---|
| 26 | (naphthyl)-CH₂CO— | sec.-butyl | tert.-butyl | m.p. 126–128° |
| 27 | —CO—CH₂—(phenyl) | tert.-butyl | tert.-butyl | m.p. 178–180° |
| 28 | —CO—CH₂—(phenyl) | tert.-pentyl | tert.-pentyl | m.p. 74–76° |
| 29 | —CO—CH₂—(phenyl)—OCH₃ | tert.-butyl | tert.-butyl | m.p. 114–116° |
| 30 | —CO—CH₂—(phenyl)—CH₃ | tert.-butyl | tert.-butyl | m.p. 106–108° |
| 31 | —CO—COOC₂H₅ | tert.-butyl | —(CH₂)₂COOCH₃ | m.p. 82–84° |
| 32 | —CO—COOC₂H₅ | tert.-butyl | tert.-butyl | m.p. 112–114° |
| 33 | —CO—COOC₂H₅ | tert.-pentyl | tert.-pentyl | m.p. 81–83° |
| 34 | —CO—COOC₂H₅ | α-dimethylbenzyl | α-dimethylbenzyl | m.p. 106–108° |
| 35 | —CO—CH=CH₂ | tert.-butyl | tert.butyl | m.p. 104–106° |
| 36 | —CO—CH=CH₂ | tert.-pentyl | tert.-pentyl | m.p. 101–103° |
| 37 | —CO—CH=CH₂ | α-dimethylbenzyl | α-dimethylbenzyl | m.p. 128–130° |
| 38 | —CO—CH=CH₂ | tert.-butyl | —CH₂CH₂COOCH₃ | m.p. 84–86° |

Example D - Esterification with acid chlorides by phase-transfer catalysis 0 1 mol of 2-[2-hydroxy-3,5-di(tert-butyl)-phenyl]-benzotriazole is dissolved in 150-200 ml of toluene. To the solution are added 20 g of NaOH dissolved in 20 ml of water (50% NaOH solution) and 0.01 mol of tetrabutylammonium hydrogen sulfate (PTC). There is immediately formed an orange-coloured emulsion, and this is heated to 40° C. At this temperature is slowly added dropwise a solution of 0.11 mol of chloroformic acid butyl ester in about 30 ml of toluene. The reaction proceeds exothermically, and from 45°-50° C. it is cooled with ice-water. At the end of the dropwise addition, the reaction solution has become light-yellow. Stirring is maintained for a further 2 hours, after which time no further starting product can be identified in the thin-layer chromatogram. The reaction solution is cooled to room temperature, and about 200 ml of water are added. The organic phase is then separated and is washed twice with 100 ml of water each time. The toluene solution is dried with sodium sulfate and is afterwards concentrated in a rotary evaporator. The light-yellow residue is recrystallised from ethanol to thus obtain 2-[2-(butoxycarbonyloxy)-3,5-di(tert-butyl)-phenyl]-benzotriazole (compound No. 39) in the form of white crystals which melt at 116°-118° C.

By variation of the acid chloride, there are obtained in an analogous manner the following phenolic esters:

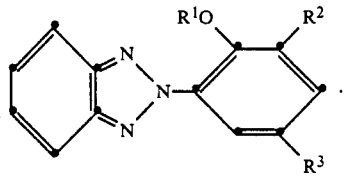

| Compound No. | R¹ | R² | R³ | Physical constants |
|---|---|---|---|---|
| 40 | —COOC₄H₉ | tert.-pentyl | tert.-pentyl | C cal. 71.0% found 70.9%<br>H cal. 8.4% found 8.3%<br>N cal. 9.5% found 9.3% |
| 41 | —COOC₄H₉ | α-dimethylbenzyl | α-dimethylbenzyl | C cal. 76.7% found 76.9%<br>H cal. 6.8% found 6.7% |

-continued

| Compound No. | R¹ | R² | R³ | Physical constants |
|---|---|---|---|---|
| 42 | —COOC$_4$H$_9$ | tert.-butyl | —CH$_2$CH$_2$COOCH$_3$ | N cal. 7.6% found 7.7%<br>C cal. 66.2% found 66.2%<br>H cal. 7.0% found 6.9% |
| 43 | —CO(CH$_2$)$_{10}$CH$_3$ | tert.-pentyl | tert.-pentyl | N cal. 9.5% found 9.7%<br>m.p. 51–54° |
| 44 | —CO(CH$_2$)$_{10}$CH$_3$ | α-dimethylbenzyl | α-dimethylbenzyl | C cal. 80.0% found 80.1%<br>H cal. 8.1% found 8.2%<br>N cal. 6.6% found 6.7% |
| 45 | —CO(CH$_2$)$_6$CH$_3$ | tert.-butyl | tert.-butyl | C cal. 74.7% found 74.9%<br>H cal. 8.7% found 8.7%<br>N cal. 9.3% found 9.3% |
| 46 | —CO(CH$_2$)$_6$CH$_3$ | tert.-pentyl | tert.-pentyl | C cal. 75.4% found 75.4%<br>H cal. 9.0% found 9.0%<br>N cal. 8.8% found 8.8% |
| 47 | —CO(CH$_2$)$_6$CH$_3$ | α-dimethylbenzyl | α-dimethylbenzyl | C cal. 79.5% found 79.5%<br>H cal. 7.5% found 7.6%<br>N cal. 7.3% found 7.4% |
| 48 | —CO(CH$_2$)$_6$CH$_3$ | tert.-butyl | —CH$_2$CH$_2$COOCH$_3$ | C cal. 70.1% found 70.2%<br>H cal. 7.7% found 7.7%<br>N cal. 8.7% found 8.8% |
| 49 | —PO(OC$_2$H$_5$)$_2$ | tert.-butyl | tert.-butyl | m.p. 118–120° |
| 50 | —PO(OC$_2$H$_5$)$_2$ | tert.-pentyl | tert.-pentyl | m.p. 93–95° |
| 51 | —PO(OC$_2$H$_5$)$_2$ | α-dimethylbenzyl | α-dimethylbenzyl | m.p. 124–126° |
| 52 | 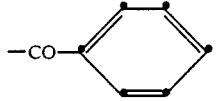 | tert.-butyl | tert.-butyl | m.p. 154–156° |
| 53 | 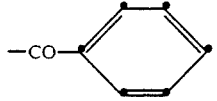 | tert.-pentyl | tert.-pentyl | m.p. 118–120° |
| 54 | 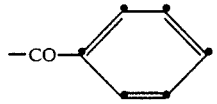 | α-dimethylbenzyl | α-dimethylbenzyl | m.p. 143–145° |
| 55 | 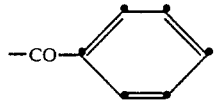 | tert.-butyl | —CH$_2$CH$_2$COOCH$_3$ | m.p. 122–124° |
| 56 | 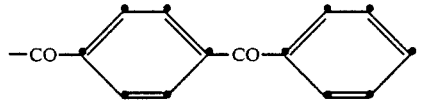 | tert.-butyl | tert.-butyl | m.p. 159–161° |
| 57 | 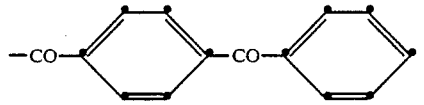 | tert.-pentyl | tert.-pentyl | m.p. 82–85° |
| 58 | 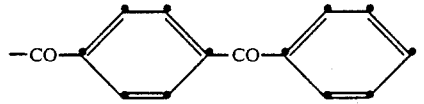 | α-dimethylbenzyl | α-dimethylbenzyl | m.p. 172–174° |
| 59 | 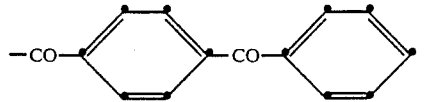 | tert.-butyl | —CH$_2$CH$_2$COOCH$_3$ | C cal. 72.7% found 72.3%<br>H cal. 5.5% found 5.6%<br>N cal. 7.4% found 7.6% |

-continued

| Compound No. | R¹ | R² | R³ | Physical constants |
|---|---|---|---|---|
| 60 | —CO—CO—⟨phenyl⟩ | tert.-butyl | tert.-butyl | m.p. 137–138° |

[Structure: bis-benzotriazole compound with adipoyl (—C(O)—(CH₂)₄—C(O)—) linker bridging two phenolic oxygens, each phenol bearing R² and R³ substituents and N-linked to a benzotriazole]

| Compound No. | R² | R³ | Physical constants |
|---|---|---|---|
| 61 | tert.-butyl | tert.-butyl | m.p. 180–182° |
| 62 | tert.-pentyl | tert.-pentyl | m.p. 109–111° |
| 63 | α-dimethylbenzyl | α-dimethylbenzyl | m.p. 201–204° |
| 64 | tert.-butyl | —CH₂CH₂COOCH₃ | m.p. 123–125° |

The coating materials according to the invention can be pigmented or unpigmented. They contain as the main component a binder which is initially a soluble resin and which, after application, is converted into an insoluble state. Curing can be effected either by heating or by a chemical reaction. Examples of such binders are: alkyl resins, acrylic resins, epoxide resins, melamine resins, urea resins, polyurethanes, polyesters or phenolic resins, and mixtures thereof with one another..

The coating material is usually applied as a solution. Coating materials with a small amount of solvent (high solids) or without solvent (with the addition of reactive diluents) have recently become of increasing importance in coating practice. In all cases, the addition of a light stabiliser can be of interest. Examples in this respect are surface lacquers for multilayer coatings, which lacquers are intended to protect the pigmented lower layer against damage by light. Surface coatings of this type are used in particular in vehicle construction. Further examples are UV protective lacquers for furniture or for plastic films or sheets. The present invention is of special importance with regard to coating materials which on application come into contact with copper or with copper alloys.

Depending on the purpose of their application, the coating materials can contain, besides pigments and solvents, other additives, for example flow-control agents, thixotropic agents, wetting agents, metal deactivators or antioxidants. They can also contain, in addition to the crypto light stabiliser according to the invention, a further light stabiliser from the class of sterically hindered amines, since these likewise do not absorb in the UV range of 330–400 nm.

The coating materials according to the invention can be applied to any desired substrates, for example to metal, glass, ceramic, wood, paper or plastic surfaces. The application is effected by the customary methods for coating materials, for example by brushing, immersion or spraying, or by electrostatic processes. The degree of activation of the light stabiliser is governed by the extent to which short-wave light acts on the coating. With a low level of irradiation, there will therefore occur a slow activation, whereas intensive irradiation will result in a rapid activation. The light stabiliser can also be artificially activated by exposing the coating before its application to UV light. This can be carried out before or after the curing of the coating. The manner in which curing is effected will depend on the nature of the employed binder, for example by heating or by oxidative curing.

The following Examples illustrate the application according to the invention of crypto light stabilisers. Except where otherwise stated, the symbol % denotes per cent by weight.

EXAMPLE 1:

Stabilisation of a two-layer metallic-effect lacquer

Aluminium sheets 0.5 mm in thickness are coated with an aluminium-pigmented base lacquer based on polyester/ cellulose acetobutyrate/melamine resin. There is then sprayed onto the wet base lacquer a clear lacquer of the following composition:

58.3 parts of Viacryl ® VC 373 (acrylic resin, Vianova, Vienna),
27.3 parts of Maprenal ® MF 590 (melamine resin, Höchst AG, Frankfurt),
1.0 part of a 1% solution of a silicone oil in xylene,
4.0 part of Solvesso ® 150 (aromatic solvent mixture),
5.4 parts of xylene, and Also added is 0.9 part of the crypto light stabiliser given in Table 1, corresponding to 2% relative to the binder. The viscosity of this clear lacquer is adjusted to 21 sec/DIN cup 4. It is applied in a dry-layer thickness of 40 μm, and is stoved at 130° C. for 30 minutes.

The specimens are in the one case weathered in a QUV rapid weatherometer (Fa. Q-Panel) and in the other case in a Xenotest ® 1200 (Fa. Heraeus) up to 5200 hours. After 800 hours in each case, the 20° gloss according to DIN 67530 is measured, and the surface of the specimens is examined for cracking under the stereomicroscope. As a basis of comparison, there is used a) an unstabilised specimen, and b) a non-blocked UV absorber of the formula

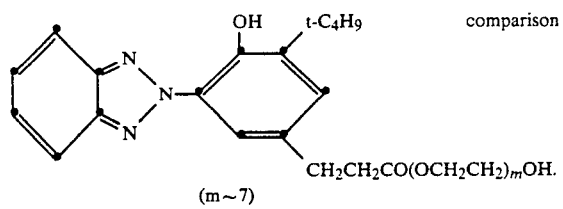

The results are summarised in Tables 1 and 2.

TABLE 1

| | QUV - 2 - Weathering | | | | |
|---|---|---|---|---|---|
| Light stabiliser | 20° gloss after | | | | Cracking noticeable after |
| | 0 | 1600 | 3200 | 4800 h | |
| none | 91 | 42 | — | — | 2800 h |
| compound No. 2 | 91 | 79 | 76 | 26 | 5200 h |
| comparison A | 90 | 81 | 69 | 29 | 5200 h |

TABLE 2

| | Xenotest ® 1200 - Weathering | | | | |
|---|---|---|---|---|---|
| Light stabiliser | 20° gloss after | | | | Cracking noticeable after |
| | 0 | 1600 | 3200 | 4800 h | |
| without | 91 | 38 | 31 | — | 3600 h |
| compound No. 2 | 91 | 68 | 54 | 31 | 5200 h |
| comparison A | 90 | 61 | 44 | 28 | 5200 h |

As can be seen from the Tables, the protective action of the crypto light stabiliser is approximately equal to that of the non-blocked light stabiliser.

EXAMPLE 2

Discoloration as a result of contact with copper

The clear lacquer described in Example 1 is brought into contact, before its application, for 48 hours with a copper sheet. The lacquer is then applied in a layer thickness of 40 μm to sheets which have been primed with a TiO$_2$-pigmented white lacquer based on polyester resin. The specimens are subsequently stoved for 30 minutes at 130° C.

The discoloration of the specimens is measured in the one case according to the Yellowness Index (YI) and in the other case according to DIN 6174 (as ΔE).

There is used as a comparison the commercial UV absorber 2-[2-hydroxy-3,5-di-(1,1-dimethylbenzyl)-phenyl]-benzotriazole =comparison B.

The results are summarised in Table 3.

TABLE 3

| Light stabiliser | YI | ΔE |
|---|---|---|
| none | 3.4 | 2.1 |
| 1% of compound No. 2 | 3.1 | 2.0 |
| 1% of comparison B | 5.8 | 3.2 |

It is seen from the Table that the free hydroxyphenylbenzotriazole causes a yellowing, whereas the crypto light stabiliser does not.

EXAMPLE 3

Storage stability of the crypto light stabilisers

Methanol solutions $5.10^{-5}$ mol/l of a benzotriazole derivative are stored for 14 days in darkness. The UV spectrum of the solutions is measured before and after storage. The solutions of the compounds Nos. 2, 5, 6, 7, 8, 11, 12, 13, 14, 15, 17 and 18 exhibit no alteration of the spectrum.

Similar blocked benzotriazole derivatives, which are unsubstituted in the ortho-position with respect to the blocked OH group, exhibit after storage an alteration of the spectrum, which indicates that a partial unblocking has occurred during storage in darkness.

EXAMPLE 4

A two-component stoving lacquer based on acrylic resin is prepared from the following components Portion A

| | |
|---|---|
| 72.8 g | of an amine-functional acrylic resin (Setalux ® 83-03 BX 55, Fa. Synthese, Netherlands), |
| 0.9 g | of a flow-control agent based on silicone oil (Baysilon ® oil, Fa. Bayer AG), and |
| 9.0 g | of xylene |
| 82.7 g | |

Portion B 17.3 g of an epoxy-functional acrylic resin (Setalux ® 83-04 5 70, Fa. Synthese, NL).

The portions A and B are combined, and a solution of the light stabiliser given in Table 4 in xylene is added. This lacquer is sprayed onto a metal sheet which is primed with a silver-metallic stoving lacquer based on polyester/ cellulose acetobutyrate/melamine resin. After exposure to the air at room temperature for one hour, the specimens are stoved for 30 minutes at 135° C. The layer thickness of the surface lacquer is about 40 μm.

The discoloration occurring on stoving is measured according to DIN 6174 as shade difference ΔE.

There are compared in each case the free hydroxybenzotriazoles and the 0-acyl compounds thereof.

TABLE 4

| Light stabiliser | ΔE |
|---|---|
| none | 0.7 |
| 2% of compound No. 8 | 1.0 |
| 2% of comparison B | 12.8 |
| 2% of compound No. 6 | 0.7 |
| 2% of comparison C | 4.4 | comparison B=2-[2-hydroxy-3,5-di(1,1-dimethylbenzyl)phenyl]-benzotriazole
comparison C=2-[2-hydroxy-3,5-di(tert-pentyl)-phenyl]benzotriazole.

EXAMPLE 5

Discoloration on weathering

The clear lacquer described in Example 1 is applied in a dry-film thickness of 40 μm to metal sheet primed white. The specimens are stoved at 130° C for 30 minutes and then weathered in a Florida apparatus for 3 months. The degree of whiteness according to DIN 6174 is measured before and after weathering, and from the result is determined in each case the shade difference ΔE. The results are summarised in Table 5.

TABLE 5

| Light stabiliser | ΔE |
|---|---|
| none | 3.2 |
| 2% of compound No. 6 | 1.0 |

TABLE 5-continued

| Light stabiliser | ΔE |
|---|---|
| 2% of compound No. 13 | 0.8 |
| 2% of compound No. 20 | 0.6 |
| 2% of compound No. 46 | 1.0 |
| 2% of compound No. 62 | 1.2 |

EXAMPLE 6

Combination with a catalyst which can be cleaved by UV

A acid-curable acrylic resin/melamine resin clear lacquer is prepared from:
- 57.3 parts of Acryloid ® AT 410 (acrylic resin, Rohm and Haas Corp., USA) (75% solids content),
- 18.0 parts of Cymel ® 301 (melamine resin, Amer. Cyanamid),
- 10.0 parts of butylacetate,
- 1.8 parts of celluose acetobutyrate CAB 551 (Eastman Chem. Corp.),
- 2.6 parts of a flow-control agent (Modaflow ®, Monsanto Corp.) and
- 10.5 parts of butanol.

The solids content of the lacquer is 65%. The lacquer is knife-coated in a dry-film thickness of 40 μm onto glass plates. The specimens are irradiated for 10 seconds with a 160 W UV-lamp, and then stoved at 120° C for 30 minutes. There is used as a curing catalyst that can be activated by UV light 1% of benzoin-p-toluenesulfonate, which cleaves off p-toluenesulfonic acid on exposure to UV light. A blocked acid catalyst of this type has the advantage that it effects no curing in darkness. It has the disadvantage that in the presence of UV-absorber light stabilisers the curing of the lacquer is incomplete. When however there is used as light stabilisers the 0-acylated benzotriazoles according to the invention, the activity of the curing catalyst is not hindered, as is shown by the following Table 6. The curing of the lacquer is assessed in these tests by measurement of the pendulum hardness according to DIN 53157. The specimens are subsequently weathered in the Xenon Weatherometer, and the percentage gloss retention is thus determined.

TABLE 6

| Light stabiliser | Gloss retention in % after weathering of | | | Pendulum hardness (sec) |
|---|---|---|---|---|
| | 1000 h | 2000 h | 3000 h | |
| none | 83 | 5 | — | 204 |
| 1% of comparison C* | 91 | 82 | 4 | 78 |
| 1% of compound No. 2 | 70 | 56 | 2 | 154 |
| 1% of compound No. 5 | 75 | 77 | 6 | 155 |
| 1% of compound No. 5 +1% of HALS** | 102 | 63 | 23 | 122 |
| 1% of compound No. 6 | 98 | 78 | 5 | 158 |

*comparison C = 2-[2-hydroxy-3,5-di-tert-pentyl-phenyl]-benzotriazole (Tinuvin ® 328)
**HALS = 8-acetyl-3-dodecyl-7,7,9,9-tetramethyl-1,3,8-triaza-spiro[4,5]decanedione-2,4 (Tinuvin ® 440)

It is seen from the above that the free benzotriazole (comparison C) does provide good protection against light but greatly reduces the curing of the lacquer. With the light stabilisers according to the invention there is however obtained both a good protection against light and satisfactory curing. The level of protection against light can be increased by the addition of a light stabiliser of the sterically hindered amine type (HALS).

What is claimed is:

1. A compound of the formula I or II

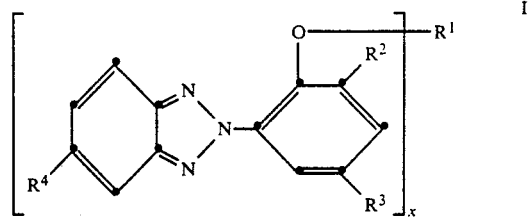

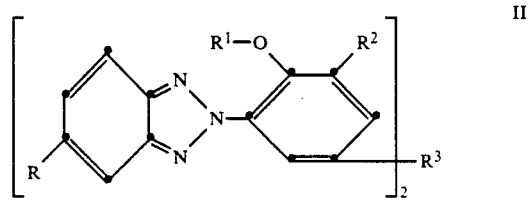

wherein x is 1, $R^1$ is an acyl group of the formula —CO—$R^5$, a sulfonyl group of the formula —$SO_2$—$R^6$, a phosphoryl group of the formula $P(O)(R^{14})(R^{15})$, $R^2$ is $C_1$–$C_{12}$-alkyl, $C_5$–$C_{12}$-cycloalkyl, phenyl, $C_7$–$C_9$-phenylalkyl, $C_3$–$C_5$-alkenyl or halogen, $R^3$ in the formula I is a group of the formula —($CH_2$)$_n$—COO$R^9$ or —($CH_2$)$_n$—CO—N($R^{10}$)($R^{11}$), and in the formula II is a divalent group of the formula:

—($CH_2$)$_n$—CO—O—($CH_2$)$_q$—O—CO—($CH_2$)$_n$—,

—($CH_2$)$_n$—CO—O—($CH_2CH_2O$)$_p$—CO—($CH_2$)$_n$-,

—($CH_2$)$_n$—CO—NH—$R^{12}$—NH—CO—($CH_2$)$_n$— or $$-(CH_2)_n-CO-O-CH_2-\underset{\underset{OR^{13}}{|}}{CH}-CH_2-O-(CH_2)_q-$$

$$-O-CH_2-\underset{\underset{OR^{13}}{|}}{CH}-CH_2-O-CO-(CH_2)_n-,$$

$R^4$ is hydrogen, halogen, $C_1$—$C_8$-alkyl, $C_7$—$C_9$-phenylalkyl, $C_1$—$C_8$-alkoxy or $C_2$—$C_8$-alkoxycarbonyl, $R^5$ is $C_1$-$C_{18}$-alkyl, $C_2$-$C_{18}$-alkenyl, —$CH_2CO$—$CH_3$, phenyl, phenyl substituted by $C_1$-$C_{12}$-alkyl, $C_1$-$C_4$-alkoxy or benzoyl, or is $C_7$-$C_{12}$-arylalkyl or $C_1$-$C_{12}$-alkoxy, $R^6$ is $C_1$-$C_{12}$-alkyl, $C_6$-$C_{10}$-aryl or $C_7$-$C_{18}$alkylaryl, $R^9$ is hydrogen, $C_1$-$C_{12}$-alkyl or a group of the formula —($CH_2CH_2O$)$_p$—$R^1$, $R^{10}$ and $R^{11}$ independently of one another are hydrogen, $C_1$–$C_{12}$-alkyl, which can be interrupted by O or N, $C_5$-$C_{12}$-cycloalkyl, $C_7$-$C_9$-phenylalkyl, $C_3$-$C_5$-alkenyl, phenyl or a 2,2,6,6-tetramethyl-4-piperidinyl radical, or $R^{10}$ and $R^{11}$ together are $C_4$-$C_6$-alkylene, -oxaalkylene or -azaalkylene, $R^{12}$ is $C_1$-$C_{12}$-alkylene, which can be interrupted by 1–3 O atoms, $R^{13}$ is $C_1$-$C_{12}$-alkyl or $C_6$-$C_{10}$-aryl, $R^{14}$ and $R^{15}$ independently of one another are each $C_1$-$C_{12}$-alkoxy, phenoxy, $C_1$-$C_{12}$-alkyl, cyclohexyl, benzyl, phenyl or tolyl, n is 1 or 2, p is a number from 1 to 10, q is a number from 2 to 12, and r is 0 or 1.

2. A compound of the formula I according to claim 1, wherein $x=1$, $R^1$ is a group of the formula —CO—$R^5$ or —$SO_2$—$R^6$, $R^2$ is $C_1$-$C_{12}$-alkyl, cyclohexyl or $C_7$-$C_9$-phenylalkyl, $R^3$ is a group —$CH_2CH_2COOR^9$, $R^4$ is hydrogen, methyl or chlorine, $R^5$ is $C_1$-$C_{12}$-alkyl, $C_2$-$C_4$-alkenyl, phenyl, benzyl or naphthylmethyl, $R^6$ is methyl, phenyl or $C_7$-$C_{15}$-alkylphenyl, and $R^9$ is $C_1$-$C_{12}$-alkyl.

3. A compound of the formula I according to claim 2, wherein $x=1$, $R^1$ is a group —CO—$R^5$ or —$SO_2$—$R^6$, $R^2$ is $C_1$-$C_8$-alkyl or α-dimethylbenzyl, $R^4$ is hydrogen or chlorine, and $R^3$, and $R^5$ and $R^6$ have the meanings defined in claim 12.

4. A compound of the formula II according to claim 1, wherein, $R^1$ is a group —CO—$R^5$ or —$SO_2$—$R^6$, $R^2$ is $C_1$-$C_8$-alkyl or α-dimethylbenzyl, $R^3$ is a group of the formula —$CH_2CH_2COO$—$(CH_2)_q$—$OCOCH_2CH_2$— or —$CH_2CH_2CONH$—$R^{12}$—$NHCOCH_2CH_2$—, $R^4$ is hydrogen or chlorine, $R^5$ is $C_1$-$C_{12}$-alkyl, $C_2$-$C_4$-alkenyl, phenyl, benzyl or naphthylmethyl, $R^6$ is methyl, phenyl or $C_7$-$C_{18}$-alkylphenyl, $R^{12}$ is $C_2C_8$-alkylene, and q is a number from 2 to 8.

* * * * *